(12) United States Patent
Cowan et al.

(10) Patent No.: US 11,801,149 B2
(45) Date of Patent: Oct. 31, 2023

(54) SURGICAL INSTRUMENT AND METHOD (71) Applicant: Warsaw Orthopedic, Inc., Warsaw, IN (US)

(72) Inventors: Benjamin D. Cowan, Memphis, TN (US); Darren L. Davis, Arlington, TN (US); Robert M. Loke, Memphis, TN (US)

( * ) Notice: Subject to any disclaimer, the term of this patent is extended or adjusted under 35 U.S.C. 154(b) by 484 days.

(21) Appl. No.: 17/066,990

(22) Filed: Oct. 9, 2020

(65) Prior Publication Data

US 2022/0110764 A1    Apr. 14, 2022

(51) Int. Cl.
*A61F 2/46*    (2006.01)

(52) U.S. Cl.
CPC ..... *A61F 2/4611* (2013.01); *A61F 2002/4627* (2013.01)

(58) Field of Classification Search
CPC ..................... A61F 2/4611; A61F 2002/4627
See application file for complete search history.

(56) References Cited

U.S. PATENT DOCUMENTS

| | | |
|---|---|---|
| 2012/0158071 A1 | 6/2012 | Jimenez et al. |
| 2013/0053966 A1 | 2/2013 | Jimenez et al. |
| 2015/0105833 A1* | 4/2015 | Simpson ............ A61B 17/8875 606/86 R |
| 2015/0265321 A1* | 9/2015 | Perry .................... A61F 2/4455 606/86 A |
| 2018/0085233 A1* | 3/2018 | Palmatier ............... A61B 34/20 |
| 2018/0311051 A1 | 11/2018 | Donaldson et al. |
| 2020/0121396 A1 | 4/2020 | Elliott et al. |

OTHER PUBLICATIONS

International Search Report and Written Opinion of the International Searching Authority (ISA/EPO) dated Dec. 6, 2021 and issued in corresponding International Application No. PCT/US2021/046800 filed Aug. 20, 2021.

* cited by examiner

*Primary Examiner* — Nicholas J Plionis
(74) *Attorney, Agent, or Firm* — Sorell, Lenna & Schmidt, LLP (57) ABSTRACT

A surgical instrument comprises a member defining a first longitudinal axis and being connectable with an image guide via a lock for orientation relative to a sensor to communicate a signal representative of a position of a spinal implant connected with the member. A rod is disposable in a co-axial orientation with the member and is engageable with the spinal implant and rotatable via an actuator to fix the spinal implant with the member. Systems, implants, spinal constructs and methods are disclosed.

20 Claims, 10 Drawing Sheets

SURGICAL INSTRUMENT AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, corpectomy, discectomy, laminectomy and implantable prosthetics. For example, fusion and fixation treatments may be performed that employ implants to restore the mechanical support function of vertebrae. Surgical instruments are employed, for example, to prepare tissue surfaces for disposal of the implants. Surgical instruments are also employed to engage implants for disposal with the tissue surfaces at a surgical site. This disclosure describes an improvement over these prior technologies.

SUMMARY

In one embodiment, a surgical instrument is provided. The surgical instrument comprises a member defining a first longitudinal axis and is connectable with an image guide via a lock for orientation relative to a sensor to communicate a signal representative of a position of a spinal implant connected with the member. A rod is disposable in a co-axial orientation with the member and is engageable with the spinal implant and rotatable via an actuator to fix the spinal implant with the member. In some embodiments, surgical systems, implants, spinal constructs and methods are provided.

In one embodiment, the surgical instrument comprises a member including a distal end, a proximal end and defines a first longitudinal axis. The proximal end defines a second axis offset relative to the first axis and includes a first mating surface. The first mating surface is connectable with a second mating surface of an image guide for orientation relative to a sensor to communicate a signal representative of a position of a spinal implant connected with the distal end. A rod is disposable in co-axial alignment with the first axis and is engageable with the spinal implant and rotatable via gearing disposed with a proximal end of the rod to fix the spinal implant with the distal end.

In one embodiment, a surgical system is provided. The surgical system comprises a spinal implant, and a surgical instrument including a distal end connected with the spinal implant and a proximal end having a first mating surface. The surgical instrument further includes a rod disposable in a co-axial orientation with the distal end. The rod is engageable with the spinal implant and rotatable via gearing disposed with a proximal end of the rod to fix the spinal implant with the distal end. An image guide has a second mating surface connectable with the first mating surface for orientation relative to a sensor to communicate a signal representative of a position of the spinal implant.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system are discussed in terms of medical devices for the treatment of musculoskeletal disorders and more particularly, in terms of a surgical system for preparing a surgical site, and a method for treating a spine. In some embodiments, the present surgical system includes a surgical instrument comprising an interbody inserter for use with a surgical navigation system for placement of an interbody device. In some embodiments, the surgical inserter includes gearing configured to rotate an end of the interbody inserter to fix a spinal implant with the interbody inserter and a lock configured to fix a surgical navigation tracker with the interbody inserter.

In some embodiments, the present surgical system includes an interbody inserter that includes an actuator configured to rotate an end of the interbody inserter to fix a spinal implant with an end of the inserter. In some embodiments, the interbody inserter includes a first longitudinal axis and a second longitudinal axis offset from the first axis. In some embodiments, a proximal end of the interbody inserter includes the second longitudinal axis. In some embodiments, the actuator includes a rod. In some embodiments, the rod is disposable in a co-axial orientation with the first longitudinal axis of the interbody inserter. In some embodiments, the rod is engageable with the spinal implant and is rotatable to fix the spinal implant with the interbody inserter.

In some embodiments, the present surgical system includes an interbody inserter having a rod with a distal end engageable with the spinal implant and an actuator that includes gearing disposed with a proximal end of the rod. In some embodiments, the distal end includes a thread and the gearing is configured to rotate the distal end into threaded fixation with a threaded surface of the spinal implant to fix the spinal implant with the inserter. In some embodiments, an outer ring is disposed with the proximal end of the rod and is configured to rotate a pinion gear fixed with the rod. In some embodiments, the outer ring is rotated in a direction, for example, clockwise, to rotate the pinion gear. In some embodiments, during rotation, circumferential teeth of the outer ring engage with circumferential teeth of the pinion gear.

In some embodiments, the interbody inserter includes an outer ring having an involute gear ring offset from the pinion gear. In some embodiments, the pinion gear is centered relative to the rod. In some embodiments, the gearing provides tightening of the spinal implant relative to the inserter. In some embodiments, the spinal implant is removable from the distal end of the rod. In some embodiments, a lock enables a navigation tracker to be independently removable from the inserter and replaceable relative to attachment of the spinal implant with the inserter.

In some embodiments, the present surgical system includes a surgical instrument comprising an interbody inserter that includes a navigation tracker. In some embodiments, the tracker is connectable to an end of the inserter. In some embodiments, the tracker is connectable to the end of the inserter via a lock. In some embodiments, the interbody inserter includes a mating surface connectable with a mating surface of the tracker. In some embodiments, the mating surface of the interbody inserter includes a circumferential flange and the mating surface of the tracker includes one or more capture prongs. In some embodiments, the mating surface of the tracker includes one or more spring loaded buttons configured to engage with the mating surface of the interbody inserter in a snap engagement. In some embodiments, the tracker is configured to communicate with a sensor of a surgical navigation system to communicate a signal representative of a position of a spinal implant. In some embodiments, the tracker is optically tracked and is disposed in a line-of-sight view to a sensor, for example, a camera. In some embodiments, the tracker provides a location of the surgical instrument in three dimensions. In some embodiments, the tracker provides a location of the surgical instrument and/or a spinal implant in two dimensions, for example, a selected plane. In some embodiments, this configuration provides indicia and/or display of implant position corresponding to an amount of manipulation, movement, translation and/or rotation of a spinal implant with tissue.

In some embodiments, the present surgical system includes a surgical instrument, for example, an implant inserter employed with a method of using a navigation system in navigated spine procedures. In some embodiments, the surgical instrument can be employed with optical-based navigation systems to facilitate surgical instrument line of sight between an instrument rotating tracker and a camera. In some embodiments, this configuration facilitates the ability to consistently track surgical instrument position throughout a surgical procedure in connection with location of a navigation camera in an operating room and for patient positioning.

In some embodiments, the present surgical system includes a surgical instrument that has a tracker and a distal/working end. In some embodiments, the tracker provides indicia and/or display of a location and angulation of the surgical instrument and its distal/working end. In some embodiments, the surgical system includes a surgical instrument having one or more image guides, which include one or more fiducial markers. In some embodiments, the fiducial marker includes a single ball-shaped marker. In some embodiments, the image guide is disposed adjacent a proximal end of the surgical instrument. In some embodiments, the image guide provides indicia and/or display of a precise rotational and/or linear position of the image guide on the surgical instrument. In some embodiments, this configuration provides indicia and/or display of an amount of manipulation, movement, translation and/or rotation of the implant with tissue.

In some embodiments, the surgical instrument includes a navigation tracker and is disposed in a direct line of sight of a sensor, which includes one or more cameras. In some embodiments, the surgical system includes an O-arm medical imaging device that digitally captures images of an anatomy. In some embodiments, the tracker communicates with a surgical navigation system to determine and/or display surgical instrument positioning relative to the anatomy.

In some embodiments, one or all of the components of the surgical system may be disposable, peel pack and/or pre packed sterile devices. One or all of the components of the surgical system may be reusable. The surgical system may be configured as a kit with multiple sized and configured components.

In some embodiments, the surgical system of the present disclosure may be employed to treat spinal disorders, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

The following discussion includes a description of a surgical system including surgical navigation, a surgical instrument, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-10, there are illustrated components of a surgical system 10.

The components of surgical system 10 can be fabricated from biologically acceptable materials suitable for medical applications, including metals, synthetic polymers and/or ceramics. For example, the components of surgical system 10, individually or collectively, can be fabricated from materials such as stainless steel alloys, aluminum, commercially pure titanium, titanium alloys, Grade 5 titanium, super-elastic titanium alloys, cobalt-chrome alloys, super-elastic metallic alloys (e.g., Nitinol, super elasto-plastic metals, such as GUM METAL®), ceramics, thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene and/or epoxy.

Various components of surgical system 10 may have material composites, including the above materials, to achieve various desired characteristics such as strength, rigidity, elasticity, compliance, biomechanical performance, durability and radiolucency or imaging preference. The components of surgical system 10, individually or collectively, may also be fabricated from a heterogeneous material such as a combination of two or more of the above-described materials. The components of surgical system 10 may be monolithically formed, integrally connected or include fastening elements and/or instruments, as described herein.

Surgical system 10 is employed, for example, with a fully open surgical procedure, a minimally invasive procedure including percutaneous techniques, and mini-open surgical techniques to deliver and introduce instrumentation and/or one or more implants at a surgical site within a body of a patient, for example, a section of a spine. In some embodiments, the surgical instrument can be configured to deliver and introduce one or more components of a spinal construct, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Figure 1:
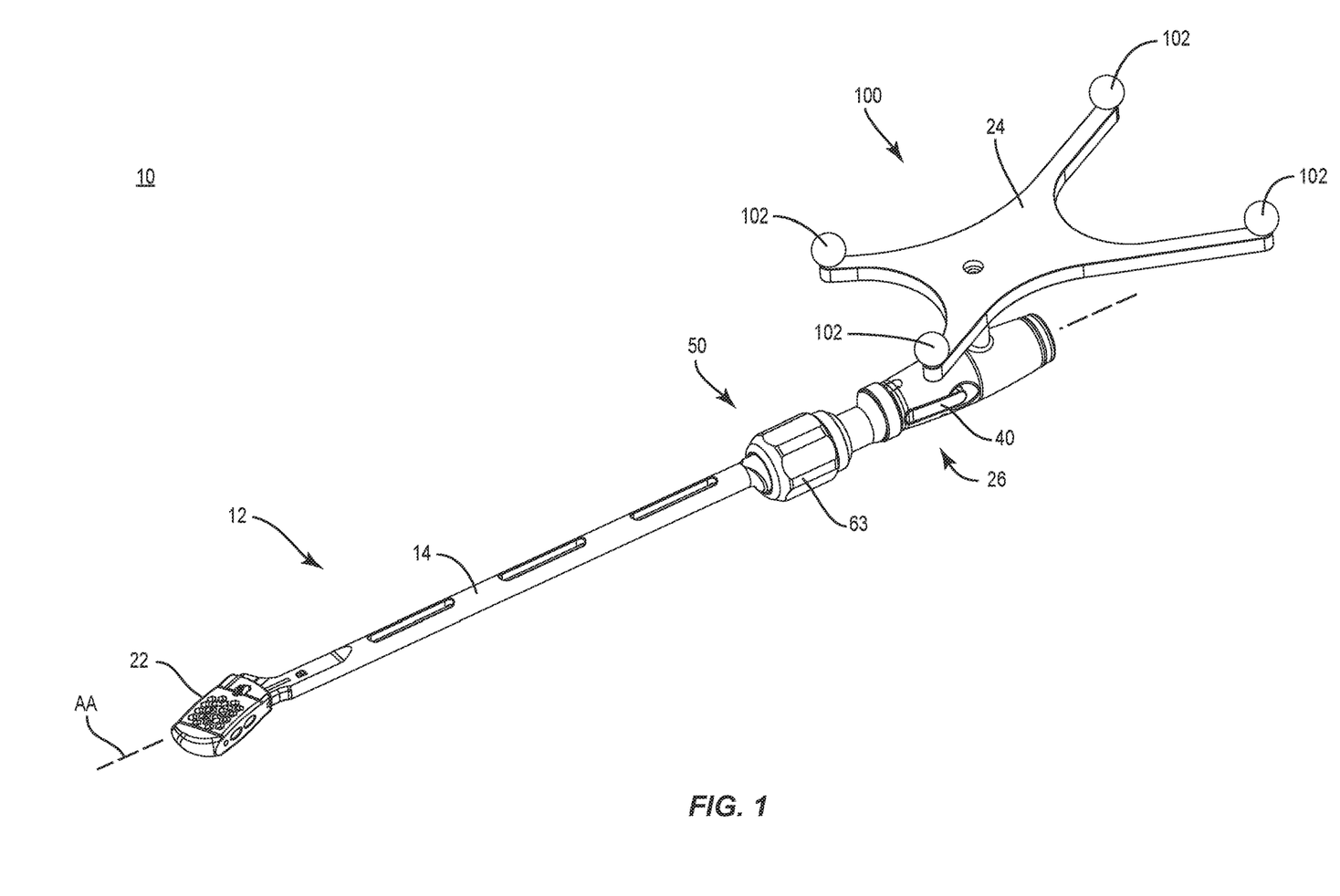
FIG. 1 is a perspective view of components of one embodiment of a surgical system in accordance with the principles of the present disclosure.
Figure 2:
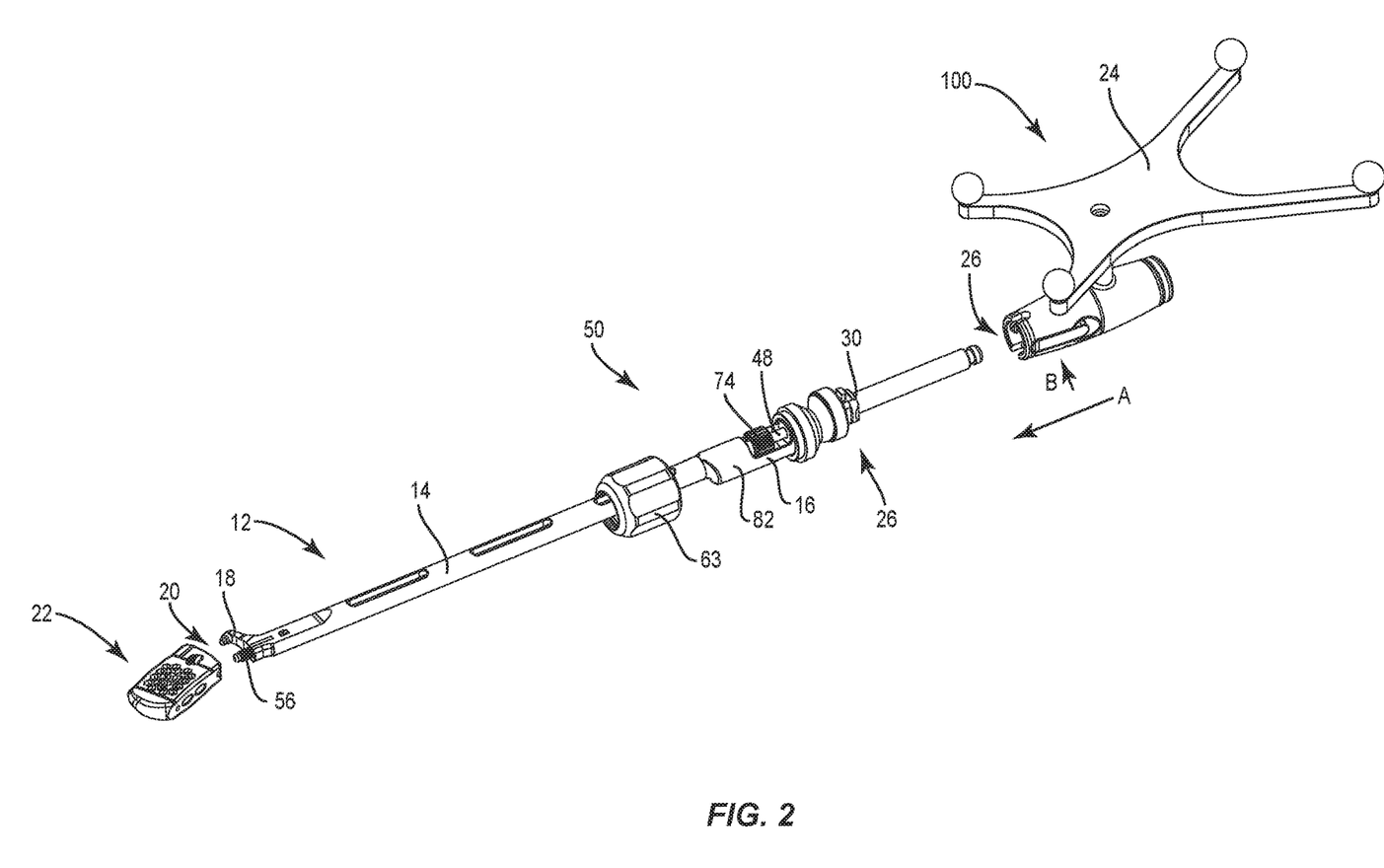
FIG. 2 is a perspective view of the components shown in FIG. 1 with parts separated.
Figure 3:
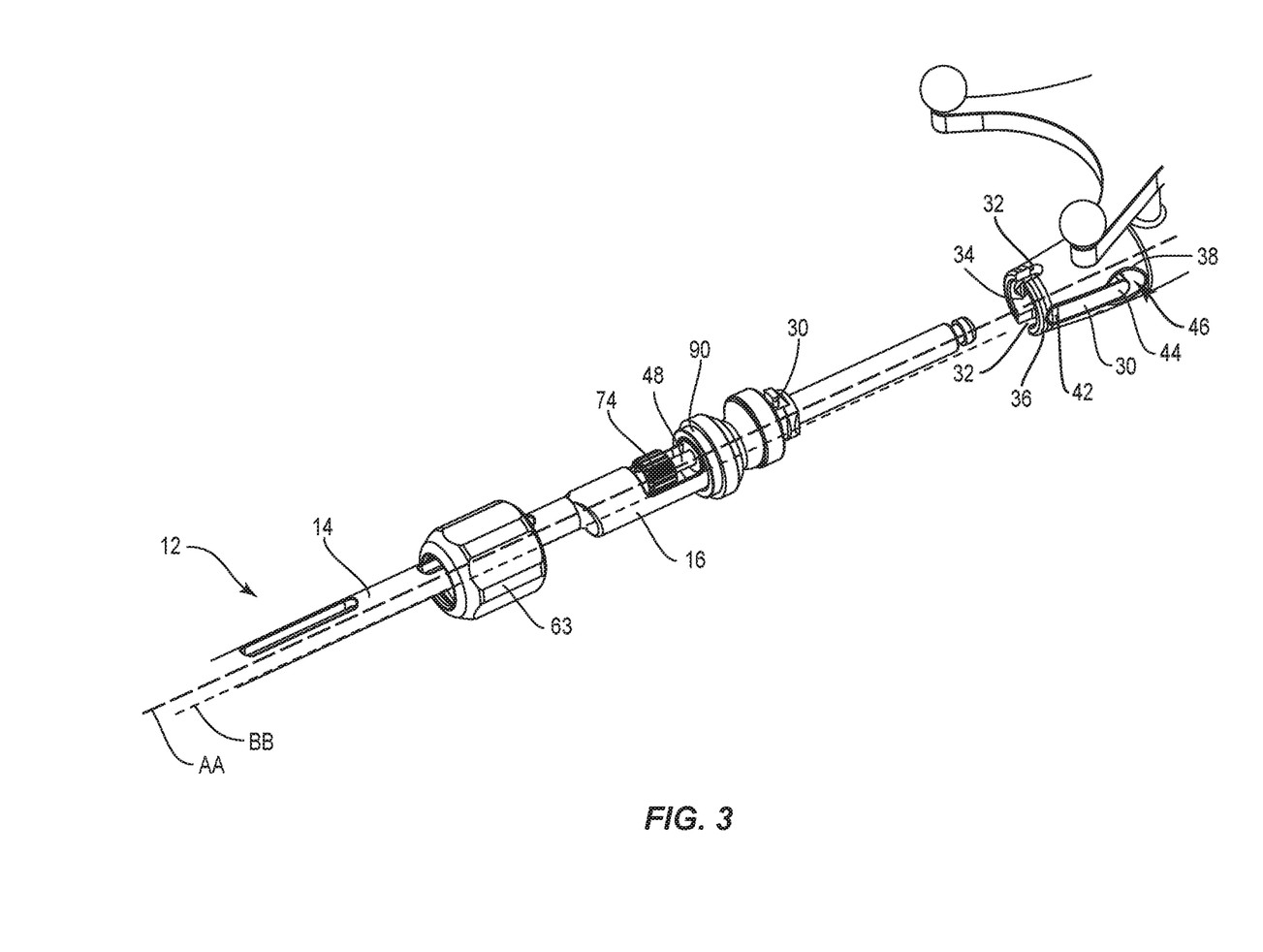
FIG. 3 is an enlarged break away view of the components shown in FIG. 1 with parts separated.

Surgical system 10 includes a surgical instrument, for example, an inserter 12. Inserter 12 includes a member, for example, a shaft 14. Shaft 14 extends between a proximal end 16 and a distal end 18 and defines a longitudinal axis AA, as shown in FIGS. 1-3. End 18 includes an engagement portion 20 configured for engagement with an interbody implant 22, as described herein. End 16 is connected with an image guide, for example, a navigation component 24. In some embodiments, shaft 14 may include alternate cross section configurations, for example, oval, oblong, triangular, square, hexagonal, polygonal, irregular, uniform, non-uniform and/or tapered.

End 16 defines a longitudinal axis BB that is offset relative to longitudinal axis AA, as shown in FIG. 3. End 16 is connected with navigation component 24 via a lock 26 for orientation relative to a sensor, for example, a sensor array 28 to communicate a signal representative of a position of implant 22, as shown in FIGS. 1-3 and 10. Lock 26 includes a mating surface including a circumferential flange 30 disposed on end 16 that is connectable with a mating surface including capturing prongs 32 disposed with navigation component 24. A surface 34 of an end 36 of navigation component 24 defines capturing prongs 32, as shown in FIG. 3. In some embodiments, circumferential flange 30 may include alternate surface configurations to enhance connection with capturing prongs 32, for example, rough, arcuate, undulating, mesh, porous, semi-porous, dimpled and/or textured. In some embodiments, circumferential flange 30 may include alternate cross section configurations, for example, oval, oblong, triangular, square, hexagonal, polygonal, irregular, uniform, non-uniform and/or tapered. In some embodiments, capturing prongs 32 may include alternate surface configurations to enhance connection with circumferential flange 30, for example, rough, arcuate, undulating, mesh, porous, semi-porous, dimpled and/or textured. In some embodiments, capturing prongs 32 include one or more prongs.

Surface 34 includes an opening 38 configured for disposal of a button 40, as shown in FIG. 3. Button 40 is configured to engage a portion of circumferential flange 30 to fix navigation component 24 with shaft 14, as shown in FIG. 1. Button 40 includes an end 42 and an end 44. A spring 46 engages end 44 of button 40 in a spring-loaded configuration. When spring 46 is disposed in an expanded position, spring 46 applies a force to button 40 such that button 40 is resiliently biased into a fixed and/or locking state. When a force is applied to button 40, for example, via manual engagement, the force overcomes the force applied by spring 46 disposing button 40 into a non-fixed and/or non-locking state. In the non-fixed and/or non-locking state, navigation component 24 can be disconnected from shaft 14. In some embodiments, button 40 may be disposed at alternate orientations relative to axis AA, for example, perpendicular and/or other angular orientations such as acute or obtuse, co-axial, offset, and/or staggered. In some embodiments, button 40 can be variously configured, for example, lever, square, rectangular, or domed shaped.

In some embodiments, navigation component 24 is connected with shaft 14 via an integral connection, friction fit, pressure fit, interlocking engagement, mating engagement, dovetail connection, clips, barbs, tongue in groove, threaded, magnetic, key/keyslot, collet and/or drill chuck.

Figure 4:
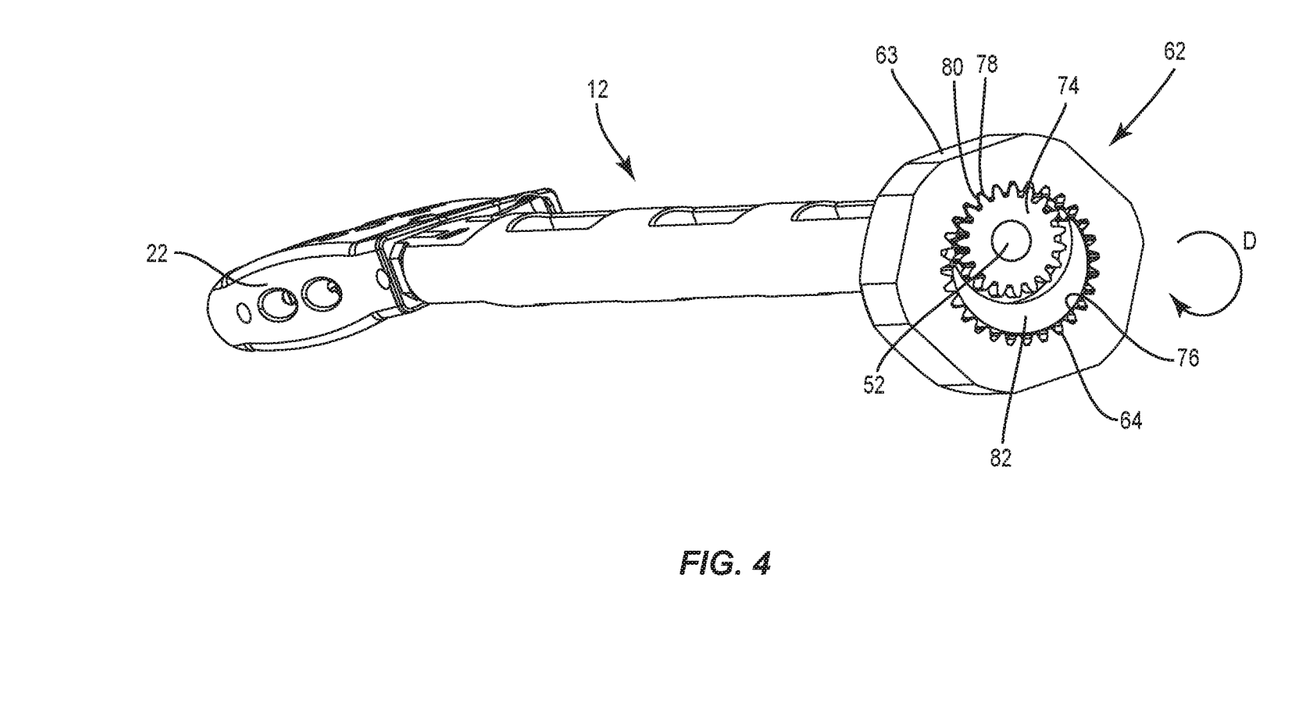
FIG. 4 is a perspective cutaway view of the components shown in FIG. 1.
Figure 7:
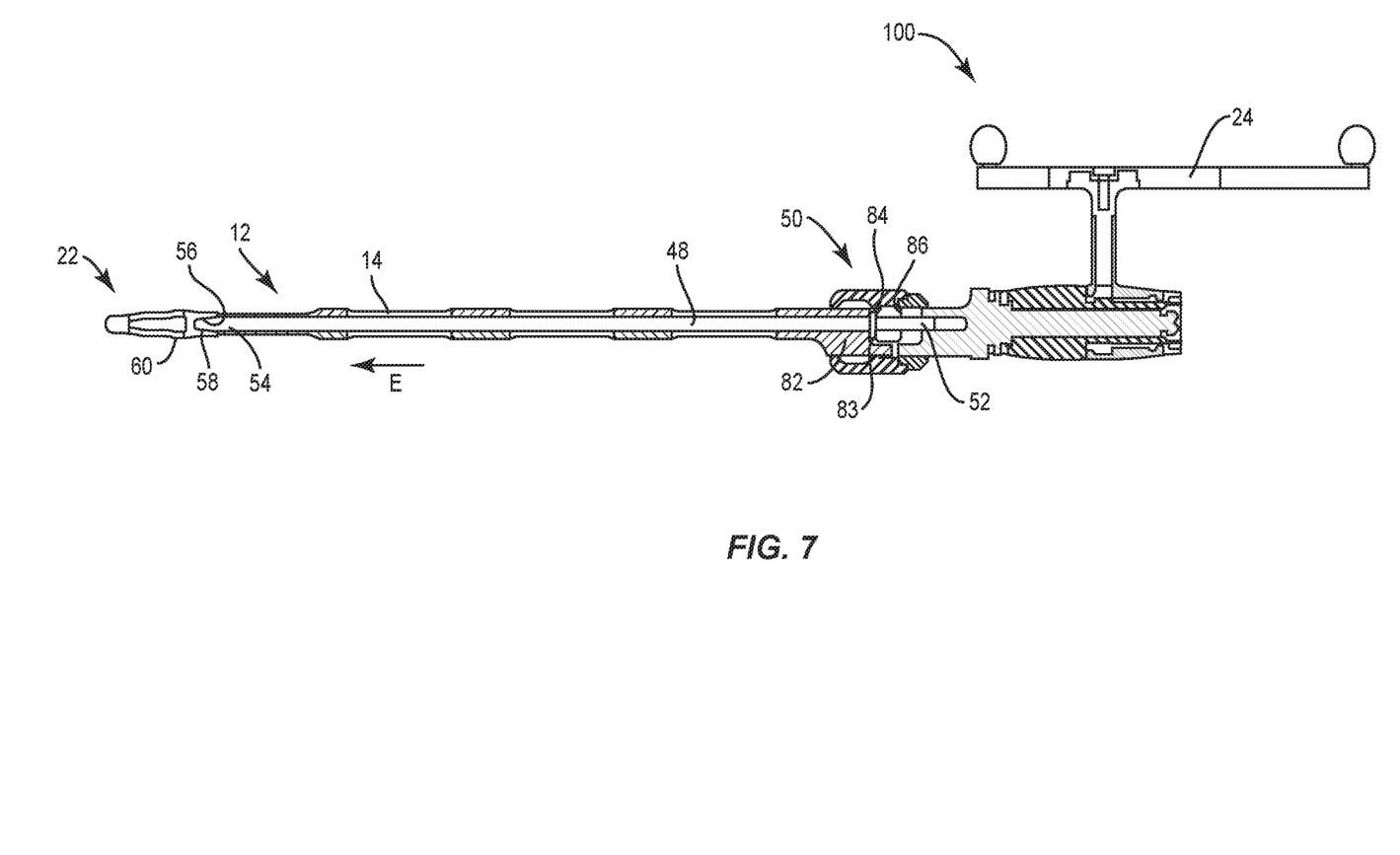
FIG. 7 is a cross section view of the components shown in FIG. 6.

A rod 48 is disposable in a co-axial orientation with longitudinal axis AA of shaft 14, as shown in FIGS. 4 and 7. Rod 48 is configured for engagement with implant 22 and is rotatable via an actuator 50 to fix implant 22 with shaft 14, as described herein. Rod 48 includes a proximal end 52 and a distal end 54, as shown in FIG. 7. In some embodiments, rod 48 may include alternate cross section configurations, for example, oval, oblong, triangular, square, hexagonal, polygonal, irregular, uniform, non-uniform and/or tapered.

End 54 includes a threaded surface 56 that is engageable in a threaded fixation with a threaded opening 58 at an end 60 of implant 22, as shown in FIGS. 2 and 7. In some embodiments, surface 56 and/or opening 58 may include one thread form configuration or a plurality of different thread form configurations. In some embodiments, the thread form configurations may include a single thread turn or a plurality of discrete threads. In some embodiments, other engaging structures may be located along surface 56 and/or opening 58, in place of or in addition to the thread form configurations discussed above, for example, a nail configuration, barbs, expanding elements, raised elements and/or spikes to facilitate engagement.

Lock 26 is disposed proximal and spaced relative to actuator 50, as shown in FIG. 1. Actuator 50 includes gearing 62 disposed with end 52, as shown in FIGS. 2-5. Gearing 62 is configured to rotate end 54 into threaded fixation with implant 22 to fix implant 22 with shaft 14. Gearing 62 includes an outer ring 63, as shown in FIGS. 3 and 4. Ring 63 includes an annular gear 64 disposed with end 52 of rod 48. Ring 63 includes an outer handle surface 72 configured for manual engagement with a user to facilitate rotation of ring 63 and gear 64, as shown in FIG. 6. In some embodiments, handle surface 72 may be disposed at alternate orientations relative to shaft 14, for example, parallel, perpendicular and/or other angular orientations such as acute or obtuse, co-axial, offset, and/or staggered. In some embodiments, handle surface 72 may include alternate surface configurations to enhance gripping of handle surface 72, for example, rough, arcuate, undulating, mesh, porous, semi-porous, dimpled and/or textured. In some embodiments, handle surface 72 may include alternate cross section configurations, for example, oval, oblong, triangular, square, hexagonal, polygonal, irregular, uniform, non-uniform and/or tapered.

Figure 5:
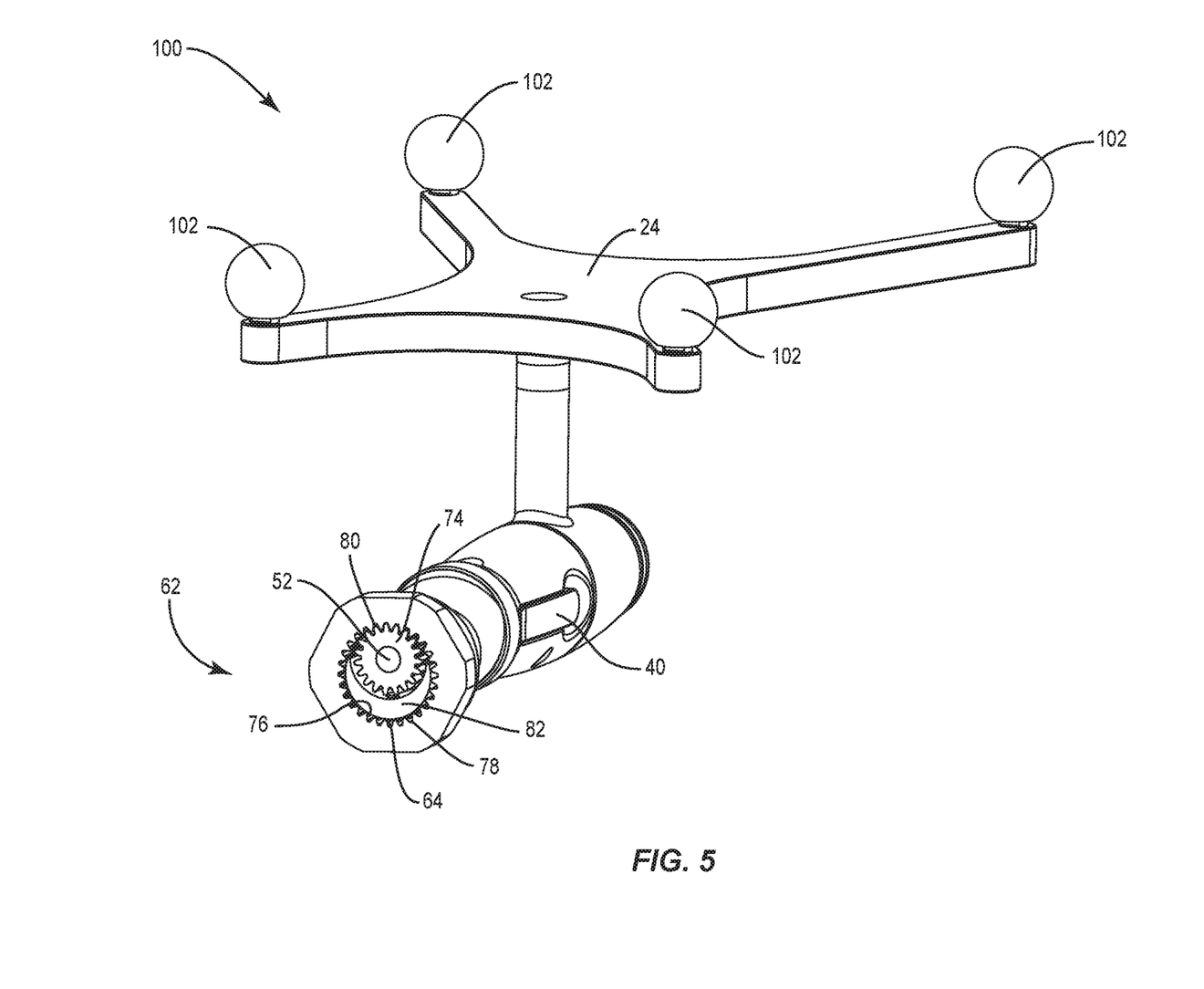
FIG. 5 is a perspective cutaway view of the components shown in FIG. 1.
Figure 6:
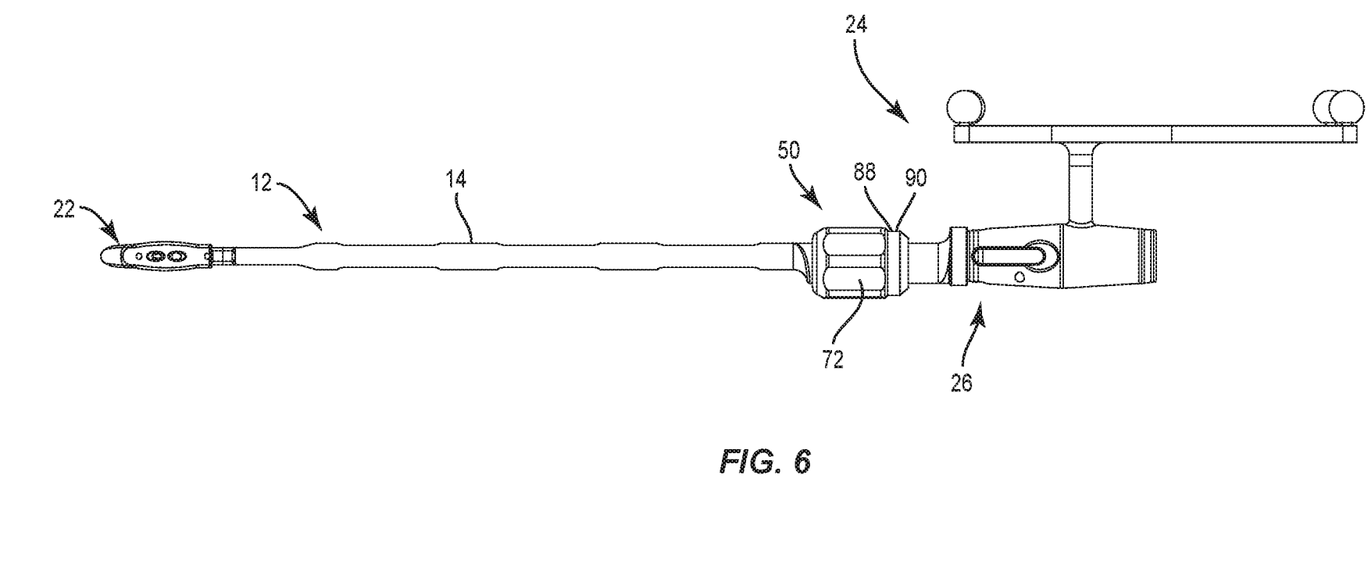
FIG. 6 is a side view of the components shown in FIG. 1.

Gear 64 is configured to rotate a pinion gear 74 that is fixed with rod 48, as shown in FIGS. 2-5. Gear 64 is rotatable and configured for engagement with gear 74 to fix implant 22 with shaft 14, as described herein. Gear 64 includes a circular inner surface 76 having circumferential teeth 78 engageable with outer circumferential teeth 80 of gear 74, as shown in FIGS. 4 and 5. In some embodiments, teeth 78 and teeth 80 each include one or more teeth.

End 16 of shaft 14 includes an extension 82 having an arcuate cross section that defines a cavity 83 with ring 63 that is configured for disposal of gear 74, as shown in FIG. 7. Gear 74 is configured for disposal within cavity 83 such that gear 64 is in co-axial alignment with longitudinal axis BB and gear 74 is in co-axial alignment with longitudinal axis AA such that only a portion of gears 64, 74 engage.

Ring 63 includes a proximal limit 84 and a distal limit 86 configured to limit axial translation of rod 48, as shown in FIG. 7. For example, as rod 48 is rotated, surface 56 is drawn into opening 58 of implant 22 via engagement between gear 64 and gear 74, which translates rod 48. Limits 84, 86 limit translation of rod 48 and provide a stop to prevent rod 48 from translating outside the selected distance provided by limits 84, 86. Limit 84 facilitates friction tightening between end 54 of rod 48 and end 60 of implant 22.

As shown in FIG. 6, ring 63 is axially fixed to a portion 90 of end 16 and rotatable relative to shaft 14 via a collar 88 of shaft 14. In some embodiments, ring 63 is fixed to collar 88 via laser welding. In some embodiments, ring 63 is laser welded to collar 88 after the components of inserter 12 are assembled. In some embodiments, ring 63 is fixed to collar 88 via alternative welding techniques, machining, interference fit and/or press fit. In some embodiments, ring 63 is fixed to collar 88 via adhesive. In some embodiments, ring 63 is configured to rotate into threaded fixation with portion 90.

To fix implant 22 with end 18 of shaft 14, ring 63 is rotated and gear 64 is rotated with ring 63. Gear 64 engages gear 74 at teeth 78, 80 to rotate gear 74 and shaft 14. Gear 64 is offset from gear 74 due to gear 64 being in co-axial alignment with longitudinal axis BB and gear 74 being in co-axial alignment with longitudinal axis AA, as shown in FIG. 3, such that gear 74 rotates when ring 63 and gear 64 are rotated. As ring 63 is rotated, limit 84 prevents ring 63 from translating proximally as end 54 of rod 48 forms a threaded fixation with opening 58 of end 60 of implant 22 to fix implant 22 with end 18 of shaft 14.

As described herein, navigation component 24 is connected with end 16. Inserter 12 is configured for disposal adjacent a surgical site such that navigation component 24 is oriented relative to sensor array 28 to facilitate communication between navigation component 24 and sensor array 28 during a surgical procedure. Navigation component 24 is configured to generate a signal representative of a position of implant 22 relative to inserter 12 and/or tissue. In some embodiments, navigation component 24 may include human readable visual indicia, human readable tactile indicia, human readable audible indicia, one or more components having markers for identification under x-ray, fluoroscopy, CT or other imaging techniques, at least one light emitting diode, a wireless component, a wired component, a near field communication component and/or one or more components that generate acoustic signals, magnetic signals, electromagnetic signals and/or radiologic signals.

Figure 10:
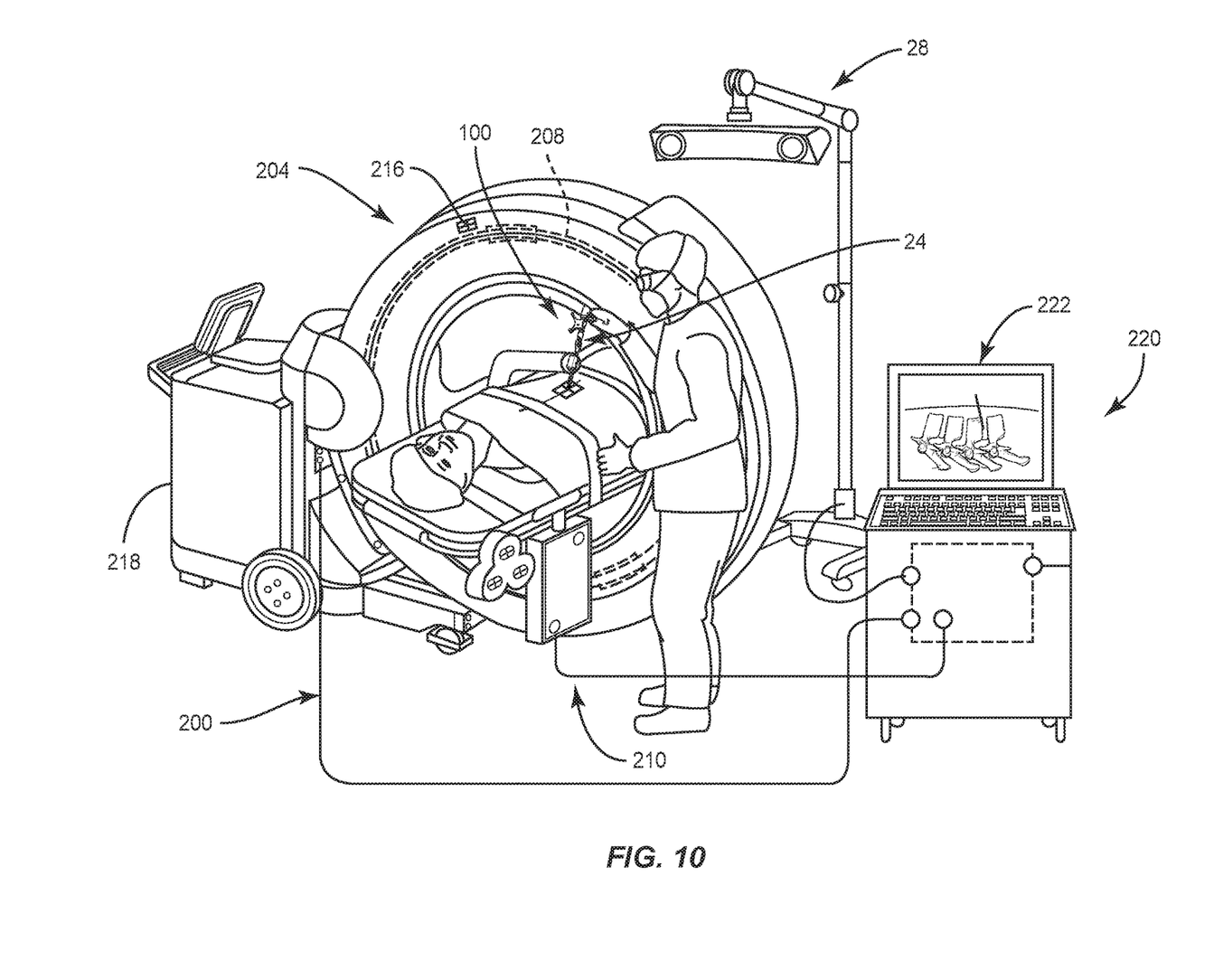
FIG. 10 is a perspective view of components of one embodiment of a surgical system in accordance with the principles of the present disclosure.

Navigation component 24 includes an emitter array 100, as shown in FIGS. 1 and 10. Emitter array 100 is configured for generating a signal to sensor array 28 of surgical navigation system 200, as shown in FIG. 10 and described herein. In some embodiments, the signal generated by emitter array 100 represents a position of implant 22 relative to inserter 12 and relative to tissue, for example, bone. In some embodiments, the signal generated by emitter array 100 represents a three-dimensional position of implant 22 relative to tissue.

In some embodiments, sensor array 28 receives signals from emitter array 100 to provide a three-dimensional spatial position and/or a trajectory of implant 22 relative to inserter 12 and/or tissue. Emitter array 100 communicates with a processor of computer 220 of navigation system 200 to generate data for display of an image on monitor 222, as described herein. In some embodiments, sensor array 28 receives signals from emitter array 100 to provide a visual representation of a position of implant 22 relative to inserter 12 and/or tissue. See, for example, similar surgical navigation components and their use as described in U.S. Pat. Nos. 6,021,343, 6,725,080, 6,796,988, the entire contents of each of these references being incorporated by reference herein.

Surgical navigation system 200 is configured for acquiring and displaying medical imaging, for example, x-ray images appropriate for a given surgical procedure. In some embodiments, pre-acquired images of a patient are collected. In some embodiments, surgical navigation system 200 can include an O-Arm® imaging device 204 sold by Medtronic Navigation, Inc. having a place of business in Louisville, Colo., USA. Imaging device 204 may have a generally annular gantry housing that encloses an image capturing portion 208.

In some embodiments, navigation system 200 comprises image capturing portion 208 that may include an x-ray source or emission portion and an x-ray receiving or image receiving portion located generally or as practically possible 180 degrees from each other and mounted on a rotor (not shown) relative to a track of image capturing portion 208. Image capturing portion 208 can be operable to rotate 360 degrees during image acquisition. Image capturing portion 208 may rotate around a central point or axis, allowing image data of the patient to be acquired from multiple directions or in multiple planes. Surgical navigation system 200 can include those disclosed in U.S. Pat. Nos. 8,842,893, 7,188,998; 7,108,421; 7,106,825; 7,001,045; and 6,940,941; the entire contents of each of these references being incorporated by reference herein.

In some embodiments, surgical navigation system 200 can include C-arm fluoroscopic imaging systems, which can generate two-dimensional views of a patient. The position of image capturing portion 208 can be precisely known relative to any other portion of imaging device 204 of navigation system 200. In some embodiments, a precise knowledge of the position of image capturing portion 208 can be used in conjunction with a tracking system 210 to determine the position of image capturing portion 208 and the image data relative to the patient.

Tracking system 210 can include various portions that are associated or included with surgical navigation system 200. In some embodiments, tracking system 210 can also include a plurality of types of tracking systems, for example, an optical tracking system that includes an optical localizer, for example, sensor array 28 and/or an EM tracking system that can include an EM localizer. Various tracking devices can be tracked with tracking system 210 and the information can be used by surgical navigation system 200 to allow for a display of a position of an item, for example, a patient tracking device, an imaging device tracking device 216, and an instrument tracking device, for example, emitter array 100, to allow selected portions to be tracked relative to one another with the appropriate tracking system.

In some embodiments, the EM tracking system can include the STEALTHSTATION® AXIEM™ Navigation System, sold by Medtronic Navigation, Inc. having a place of business in Louisville, Colo. Exemplary tracking systems are also disclosed in U.S. Pat. Nos. 8,057,407, 5,913,820, 5,592,939, the entire contents of each of these references being incorporated by reference herein.

Fluoroscopic images taken are transmitted to a computer 218 where they may be forwarded to computer 220. Image transfer may be performed over a standard video connection or a digital link including wired and wireless. Computer 220 provides the ability to display, via monitor 222, as well as save, digitally manipulate, or print a hard copy of the received images. In some embodiments, images may also be displayed to the surgeon through a heads-up display.

In some embodiments, surgical navigation system 200 provides for real-time tracking of the position of implant 22 relative to inserter 12 and/or tissue. Sensor array 28 is located in such a manner to provide a clear line of sight with emitter array 100, as described herein. In some embodiments, fiducial markers 102 of emitter array 100 communicate with sensor array 28 via infrared technology. Sensor array 28 is coupled to computer 220, which may be programmed with software modules that analyze signals transmitted by sensor array 28 to determine the position of each object in a detector space.

Figure 8:
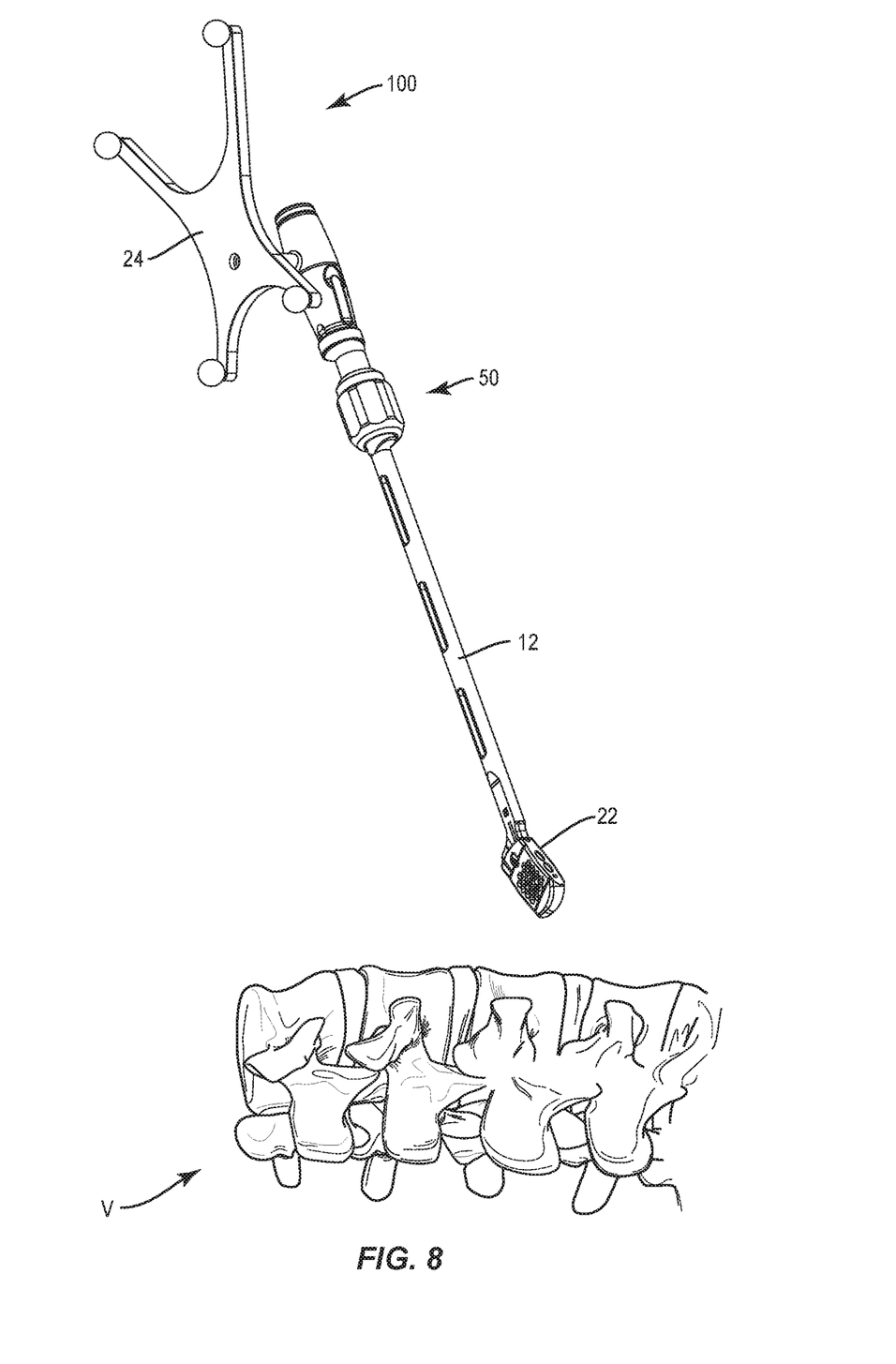
FIG. 8 is a perspective view of components of one embodiment of a surgical system in accordance with the principles of the present disclosure disposed with vertebrae.
Figure 9:
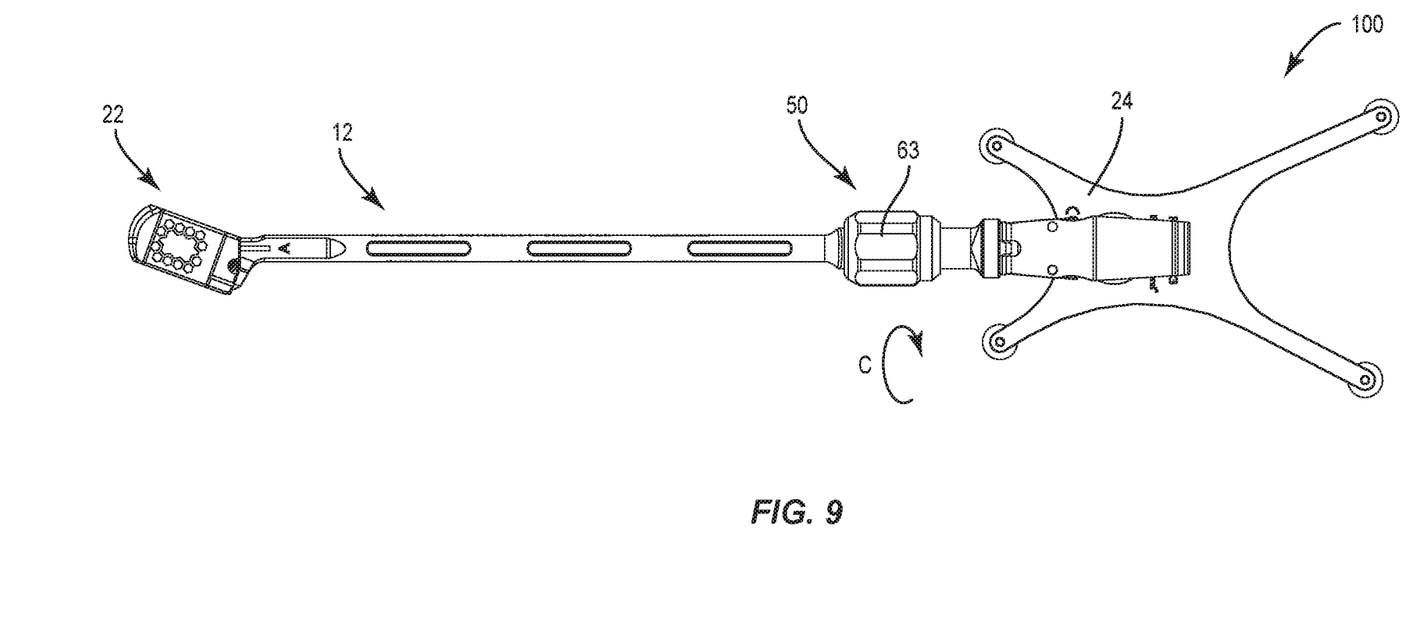
FIG. 9 is a plan view of the components shown in FIG. 8.

In assembly, operation and use, surgical system 10, similar to the systems and methods described herein, is employed with a surgical procedure for treatment of a spinal disorder affecting a section of a spine of a patient, as discussed herein. For example, the components of surgical system 10 can be used with a surgical procedure for treatment of a condition or injury of an affected section of the spine including vertebrae V, as shown in FIGS. 8-10. In some embodiments, one or all of the components of surgical system 10 can be delivered or implanted as a pre-assembled device or can be assembled in situ. Surgical system 10 may be completely or partially revised, removed or replaced.

The components of surgical system 10 can be employed with a surgical treatment of an applicable condition or injury of an affected section of a spinal column and adjacent areas within a body, for example, vertebrae. In some embodiments, the components of surgical system 10 may be employed with one or a plurality of vertebra. To treat a selected section of vertebrae V, a medical practitioner obtains access to a surgical site including vertebrae in any appropriate manner, such as through incision and retraction of tissues. In some embodiments, the components of surgical system 10 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for delivery of components of surgical system 10 including inserter 12 and implant 22, as described herein, adjacent an area within the patient's body, for example, vertebrae. In some embodiments, a preparation instrument (not shown) can be employed to prepare tissue surfaces of vertebrae, as well as for aspiration and irrigation of a surgical region.

Navigation component 24 is connected with end 16 of shaft 14 via lock 26. For example, end 36 of navigation component 24 is translated in a direction, for example, a direction shown by arrow A in FIG. 2, to connect navigation component 24 with end 16. Capturing prongs 32 connect with circumferential flange 30 when navigation component 24 is translated in the direction of arrow A, and button 40 is manually depressed in a direction, for example, a direction shown by arrow B in FIG. 2, to engage a portion of circumferential flange 30. Spring 46 is disposed in an expanded position to apply a force to button 40 such that button 40 is resiliently biased into a fixed and/or locking state.

Inserter 12 is aligned with implant 22 for disposal in an insertion or delivery orientation. For example, end 18 of shaft 14 is positioned adjacent to end 60 of implant 22, as shown in FIG. 2. Ring 63 is rotated in a clockwise direction shown by arrow C in FIG. 9, and gear 64 is rotated with ring 63. Gear 64 engages gear 74 at teeth 78, 80 to rotate gear 74 and shaft 14, in a clockwise direction shown by arrow D in FIG. 4. Gear 74 rotates as ring 63 and gear 64 are rotated due to gear 64 being offset from gear 74 due to gear 64 being in co-axial alignment with longitudinal axis BB and gear 74 being in co-axial alignment with longitudinal axis AA. As ring 63 is rotated, shaft 14 can translate, in a direction shown by arrow E in FIG. 7, and translation of shaft 14 is prevented when limit 84 is reached. Rotation and translation of shaft 14 creates a threaded fixation with implant 22 via threaded surface 56 of end 54 and threaded opening 58 of end 60 of implant 22.

Inserter 12 is manipulated to deliver implant 22 to an intervertebral space. Sensor array 28 receives signals from navigation component 24 to provide a three-dimensional spatial position and/or a trajectory of inserter 12 and/or implant 22 relative to the intervertebral space and/or a depth of inserter 12 and/or implant 22 within the intervertebral space for display on monitor 222. Inserter 12 is disengageable from interbody implant 22. In some embodiments, implant 22 provides height restoration between vertebral bodies, decompression, restoration of sagittal and/or coronal balance and/or resistance of subsidence into vertebral endplates.

In some embodiments, one or more of the components of surgical system 10, as described herein, may include and/or be connected with various instruments including the configuration of the present disclosure, for example, inserters, extenders, reducers, spreaders, distractors, blades, retractors, clamps, forceps, elevators and drills, which may be alternately sized and dimensioned, and arranged as a kit.

In some embodiments, surgical system 10 includes an agent, which may be disposed, packed or layered within, on or about the components and/or surfaces of surgical system 10. In some embodiments, the agent may include bone growth promoting material, for example, bone graft to enhance fixation with vertebrae V. The components of surgical system 10 can be made of radiolucent materials such as polymers. Radiomarkers may be included for identification under x-ray, fluoroscopy, CT or other imaging techniques. In some embodiments, the agent may include one or a plurality of therapeutic agents and/or pharmacological agents for release, including sustained release, to treat, for example, pain, inflammation and degeneration. Upon completion of the procedure, the surgical instruments, assemblies and non-implanted components of surgical system 10 are removed from the surgical site and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument comprising:
a member defining a first longitudinal axis and being connectable with an image guide via a lock for orientation relative to a sensor to communicate a signal representative of a position of a spinal implant connected with the member; and
a rod being disposable in a co-axial orientation with the member, the rod being engageable with the spinal implant and rotatable via an actuator to fix the spinal implant with the member,
the actuator including gearing, the gearing having an inner surface including at least one tooth and the rod having a proximal end including a pinion gear engageable with the at least one tooth,
the member including a proximal end having an extension being offset relative to the first longitudinal axis to define a cavity with the inner surface of the actuator, the cavity being configured for disposal of the pinion gear such that the extension is disposed between the at least one tooth of the gearing and the pinion gear.

2. A surgical instrument as recited in claim 1, wherein the rod includes a distal end engageable with the spinal implant and the gearing is disposed with the proximal end of the rod.

3. A surgical instrument as recited in claim 2, wherein the distal end includes a thread and the gearing is configured to rotate the distal end into threaded fixation with the spinal implant to fix the spinal implant with the member.

4. A surgical instrument as recited in claim 1, wherein the gearing includes an outer ring disposed with the proximal end of the rod and being configured to rotate the pinion gear.

5. A surgical instrument as recited in claim 4, wherein the outer ring is rotatable and configured for engagement with the pinion gear to fix the spinal implant with the member.

6. A surgical instrument as recited in claim 5, wherein the outer ring includes a circular inner surface.

7. A surgical instrument as recited in claim 4, wherein the extension includes an arcuate cross section.

8. A surgical instrument as recited in claim 4, wherein the outer ring includes an annular gear engageable with the pinion gear.

9. A surgical instrument as recited in claim 4, wherein the outer ring includes an outer handle surface.

10. A surgical instrument as recited in claim 4, wherein the outer ring is axially fixed with and rotatable relative to the member.

11. A surgical instrument as recited in claim 4, wherein the outer ring includes a proximal limit and a distal limit configured to limit axial translation of the rod.

12. A surgical instrument as recited in claim 1, wherein the lock is disposed proximal and spaced relative to the actuator.

13. A surgical instrument as recited in claim 1, wherein the proximal end of the member includes a first mating surface of the lock connectable with a second mating surface of the lock disposed with the image guide.

14. A surgical instrument as recited in claim 13, wherein the first mating surface includes a circumferential flange and the second mating surface includes at least one capture prong.

15. A surgical instrument as recited in claim 1, wherein the proximal end of the member defines a second longitudinal axis offset relative to the first longitudinal axis.

16. A surgical instrument comprising:
a member including a distal end, a proximal end and defining a first longitudinal axis extending between the distal end and the proximal end, the proximal end defining a second longitudinal axis offset relative to the first longitudinal axis and including a first mating surface,
the first mating surface being connectable with a second mating surface of an image guide for orientation relative to a sensor to communicate a signal representative of a position of a spinal implant connected with the distal end; and a rod being disposable in co-axial alignment with the first longitudinal axis, the rod being engageable with the spinal implant and rotatable via an actuator disposed with a proximal end of the rod to fix the spinal implant with the distal end, the actuator having an inner surface including at least one tooth and the proximal end of the rod including a pinion gear engageable with the at least one tooth, the proximal end of the member having an extension being offset relative to the first longitudinal axis to define a cavity with the inner surface of the actuator, the cavity being configured for disposal of the pinion gear such that the extension is disposed between the at least one tooth of the actuator and the pinion gear.

17. A surgical instrument as recited in claim 16, wherein actuator includes an outer ring disposed with the rod and being configured to rotate the pinion gear.

18. A surgical instrument as recited in claim 17, wherein the extension includes an arcuate cross section.

19. A surgical system comprising:
a spinal implant;
a surgical instrument including a distal end connected with the spinal implant and a proximal end having a first mating surface, the surgical instrument further including a rod being disposable in a co-axial orientation with the distal end, the rod being engageable with the spinal implant and rotatable via an actuator disposed with a proximal end of the rod to fix the spinal implant with the distal end; and an image guide having a second mating surface connectable with the first mating surface for orientation relative to a sensor to communicate a signal representative of a position of the spinal implant, the actuator having an inner surface including at least one tooth and the proximal end of the rod including a pinion gear engageable with the at least one tooth, the proximal end of the surgical instrument having an extension being offset relative to a first longitudinal axis that extends between the proximal end and the distal end of the surgical instrument, the extension defining a cavity with the inner surface of the actuator, the cavity being configured for disposal of the pinion gear such that the extension is disposed between the at least one tooth of the actuator and the pinion gear.

20. A surgical system as recited in claim 19, wherein the actuator includes an outer ring disposed with the rod and being configured to rotate the pinion gear.

* * * * *